US010550365B2

(12) United States Patent
Biggs et al.

(10) Patent No.: US 10,550,365 B2
(45) Date of Patent: Feb. 4, 2020

(54) CELLULAR RESPONSE TO SURFACE WITH NANOSCALE HETEROGENEOUS RIGIDITY

(71) Applicant: The Trustees of Columbia University in the City of New York, New York, NY (US)

(72) Inventors: Manus J. P. Biggs, Galway (IE); Ryan Cooper, Oak Ridge, TN (US); Jinyu Liao, New York, NY (US); Teresa Anne Fazio, Poughkeepsie, NY (US); Carl Fredrik Oskar Dahlberg, Stockholm (SE); Jeffrey William Kysar, New York, NY (US); Samuel Jonas Wind, White Plains, NY (US)

(73) Assignee: The Trustees of Columbia University in the City of New York, New York, NY (US)

(*) Notice: Subject to any disclaimer, the term of this patent is extended or adjusted under 35 U.S.C. 154(b) by 372 days.

(21) Appl. No.: 15/483,754

(22) Filed: Apr. 10, 2017

(65) Prior Publication Data
US 2017/0275585 A1 Sep. 28, 2017

Related U.S. Application Data

(63) Continuation of application No. 14/523,586, filed on Oct. 24, 2014, now abandoned, which is a
(Continued)

(51) Int. Cl.
*C12N 5/00* (2006.01)
*C12N 5/0775* (2010.01)

(52) U.S. Cl.
CPC ......... *C12N 5/0068* (2013.01); *C12N 5/0663* (2013.01); *C12N 2533/30* (2013.01);
(Continued)

(58) Field of Classification Search
CPC ................ B29C 33/424; B29C 33/405; B29C 2033/426; B81C 1/00444; B81C 1/0046;
(Continued)

(56) References Cited

U.S. PATENT DOCUMENTS 4,981,912 A 1/1991 Kurihara
6,787,358 B2 9/2004 Nelles et al.
(Continued)

FOREIGN PATENT DOCUMENTS

WO WO-2004091763 A2 10/2004
WO WO-2007048662 A1 * 5/2007 ......... B29C 35/0266
(Continued)

OTHER PUBLICATIONS

"U.S. Appl. No. 12/936,025, Advisory Action dated May 22, 2014", 5 pgs.
(Continued)

*Primary Examiner* — Michael P Wieczorek
(74) *Attorney, Agent, or Firm* — Schwegman Lundberg & Woessner, P.A.

(57) ABSTRACT

An elastomeric substrate comprises a surface with regions of heterogeneous rigidity, wherein the regions are formed by exposing the elastomeric substrate to an energy source to form the regions such that the regions include a rigidity pattern comprising spots.

12 Claims, 13 Drawing Sheets
(13 of 13 Drawing Sheet(s) Filed in Color)

Related U.S. Application Data continuation-in-part of application No. 12/936,025, filed as application No. PCT/US2009/002069 on Apr. 2, 2009, now abandoned.

(60) Provisional application No. 61/895,068, filed on Oct. 24, 2013, provisional application No. 61/072,717, filed on Apr. 2, 2008.

(52) U.S. Cl.
CPC ...... *C12N 2535/00* (2013.01); *C12N 2535/10* (2013.01); *C12N 2537/10* (2013.01)

(58) Field of Classification Search
CPC ...... B82B 3/00; C12N 5/0068; C12N 5/0663; C12N 2533/30; C12N 2533/00; C12N 2533/10; C12N 2537/10
USPC .............................. 264/485, 482, 494, 496
See application file for complete search history.

(56) References Cited

U.S. PATENT DOCUMENTS

| | | | |
|---|---|---|---|
| 6,872,439 | B2 | 3/2005 | Fearing et al. |
| 7,143,709 | B2 | 12/2006 | Brennan et al. |
| 7,211,209 | B2 | 5/2007 | Kim et al. |
| 7,891,636 | B2* | 2/2011 | Zhang ............. B29C 33/3857 249/134 |
| 2003/0207099 | A1 | 11/2003 | Gillmor et al. |
| 2004/0115793 | A1 | 6/2004 | Rasmussen et al. |
| 2006/0051329 | A1 | 3/2006 | Lee et al. |
| 2006/0166128 | A1 | 7/2006 | Gogolides et al. |
| 2006/0286488 | A1 | 12/2006 | Rogers et al. |
| 2007/0000866 | A1 | 1/2007 | Ryan et al. |
| 2007/0254005 | A1 | 11/2007 | Pathak et al. |
| 2008/0187995 | A1 | 8/2008 | Murphy et al. |
| 2008/0193684 | A1* | 8/2008 | Buhring ............. B29C 35/0266 428/31 |
| 2008/0241926 | A1 | 10/2008 | Lee et al. |
| 2009/0028755 | A1 | 1/2009 | Jedrzejewski et al. |
| 2011/0095165 | A1 | 4/2011 | Rule et al. |
| 2011/0111178 | A1 | 5/2011 | Wind et al. |
| 2013/0010364 | A1 | 1/2013 | Hebrink et al. |
| 2015/0125957 | A1 | 5/2015 | Biggs et al. |

FOREIGN PATENT DOCUMENTS

| | | |
|---|---|---|
| WO | WO-2007057693 A2 | 5/2007 |
| WO | WO-2009015296 A1 | 1/2009 |
| WO | WO-2009123739 A1 | 10/2009 |

OTHER PUBLICATIONS

"U.S. Appl. No. 12/936,025, Examiner Interview Summary dated Apr. 28, 2014", 3 pgs.

"U.S. Appl. No. 12/936,025, Final Office Action dated Jan. 3, 2014", 10 pgs.

"U.S. Appl. No. 12/936,025, Final Office Action dated Dec. 12, 2014", 20 pgs.

"U.S. Appl. No. 12/936,025, Non Final Office Action dated Apr. 25, 2013", 22 pgs.

"U.S. Appl. No. 12/936,025, Non Final Office Action dated Jul. 10, 2014", 16 pgs.

"U.S. Appl. No. 12/936,025, Response filed Mar. 1, 2013 to Restriction Requirement dated Dec. 6, 2012", 7 pgs.

"U.S. Appl. No. 12/936,025, Response filed May 1, 2014 to Final Office Action dated Jan. 3, 2014", 14 pgs.

"U.S. Appl. No. 12/936,025, Response filed Oct. 10, 2014 to Non Final Office Action dated Jul. 10, 2014", 14 pgs.

"U.S. Appl. No. 12/936,025, Response filed Oct. 25, 2013 to Non Final Office Action dated Apr. 25, 2013", 22 pgs.

"U.S. Appl. No. 12/936,025, Restriction Requirement dated Dec. 6, 2012", 6 pgs.

"U.S. Appl. No. 14/523,586, Restriction Requirement dated Oct. 19, 2016", 8 pgs.

"International application serial No. PCT/US2009/02069, International Search Report dated Jul. 2, 2009", 2 pgs.

"International application serial No. PCT/US2009/02069, Written Opinion dated Jul. 2, 2009", 9 pgs.

Bolte, S., et al., "A guided tour into subcellular colocalization analysis in light microscopy", J. Microsc., 224(Pt. 3), (2006), 20 pgs.

Engler, A. J., et al., "Matrix elasticity directs stem cell lineage specification.", Cell, 126(4), (Aug. 25, 2006), 677-689.

Manders, E. M., et al., "Dynamics of three-dimensional replication patterns during the S-phase, analysed by double labelling of DNA and confocal microscopy", J. Cell. Sci., 103(Pt. 3), (1992), 857-862.

Paszek, M. J, et al., "Tensional homeostasis and the malignant phenotype.", Cancer Cell., 8(3), (Sep. 2005), 241-54.

Ramser, K., et al., "A microfluidic system enabling Raman measurements of the oxygenation cycle in single optically trapped red blood cells.", Lab on a Chip, 5(4), (2005), 431-436.

Russell, M. T, et al., "Microscale features and surface chemical functionality patterned by electron beam lithography: a novel route to poly(dimethylsiloxane) (PDMS) stamp fabrication.", Langmuir, 22(15), (2006), 6712-6718.

Saez, A., et al., "Rigidity-driven growth and migration of epithelial cells on microstructured /' nisotropic substrates", Proc. Natl. Acad. Sci. USA, 104(20), (May 15, 2007), 8281-8286.

\* cited by examiner

INCREASING SPOT RIGIDITY

INCREASING SPOT RIGIDITY

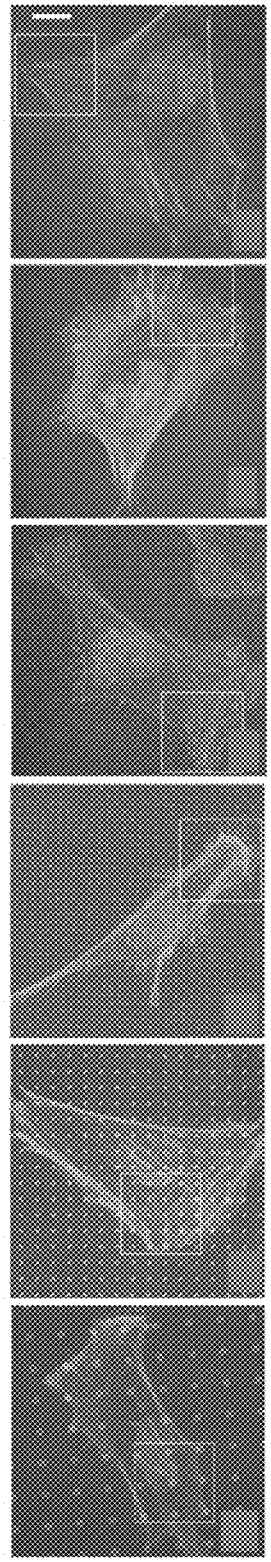
FIG. 7A  FIG. 7B  FIG. 7C  FIG. 7D  FIG. 7E  FIG. 7F

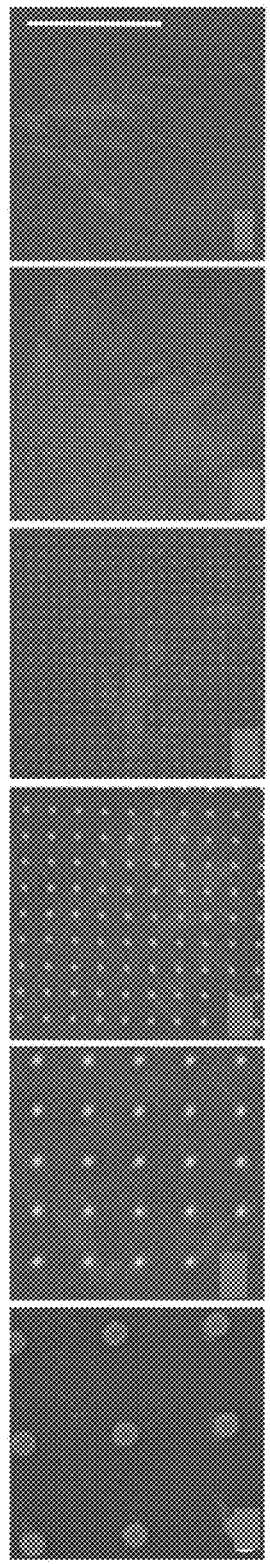

CELLULAR RESPONSE TO SURFACE WITH NANOSCALE HETEROGENEOUS RIGIDITY

CROSS-REFERENCE TO RELATED APPLICATIONS

This application is a continuation of and claims the benefit of priority under 35 U.S.C. § 120 to U.S. patent application Ser. No. 14/523,586, filed on Oct. 24, 2014, which claims the benefit of priority under 35 U.S.C. § 119(e) to U.S. Provisional Application Ser. No. 61/895,068, filed on Oct. 24, 2013, and is a continuation-in-part under 35 U.S.C. § 120 of U.S. patent application Ser. No. 12/936,025, which is a U.S. National Stage Filing under 35 U.S.C. § 371 from International Application No. PCT/US2009/002069, filed Apr. 2, 2009 and published as WO 1009/123739 A1 on Oct. 8, 2009, which claimed priority under 35 U.S.C. § 119(e) to U.S. Provisional Application Ser. No. 61/072,717, filed on Apr. 2, 2008, each of which are incorporated herein by reference in their entireties.

STATEMENT REGARDING FEDERALLY SPONSORED RESEARCH OR DEVELOPMENT

This invention was made with government support under grants CHE0641523 and EY016586 awarded by the NSF and NIH. The government has certain rights in the invention.

BACKGROUND

The physical properties of a cell's environment are important factors in determining cell behavior and ultimately, phenotype. Among these factors, matrix rigidity can affect cell growth, differentiation and adhesion and motility. Alteration of the cellular rigidity sensing mechanism can be implicated in malignant transformation and tumerogenesis. Many aspects of the cellular rigidity-sensing mechanism are of interest, particularly in reference to tactile cell sensing of discrete localized areas of increased or decreased rigidity.

As well as responding to biochemical signals, cells can directly probe the physical properties of the extracellular environment around them, such as to determine force, shape, geometry and stiffness of the extracellular environment. The cells can probe the extracellular environment by adhering and initiating matrix deformation by the application of cellular tractive forces. Matrix or tissue elasticity can have a role in regulating multiple cell processes, including cell adhesion, cell migration, and differential function, through cell-generated actomyosin interactive forces regulated by a dynamic feedback mechanism.

The sensitivity of cells to the mechanical properties of the extracellular matrix can be attributable to the mechanosensitive nature of the molecules involved in the structures of cell adhesion. Among adhesive structures, focal adhesions appear to be the most prominent, demonstrating correlation between focal adhesion reinforcement and sustained force exhibiting a constant stress. This mechanosensitivity may be regulated by a conserved local mechanism in which subcellular forces induce an elastic deformation of transmembrane integrin regions, triggering conformational and organizational changes and resulting in integrin activation, which in turn can uncover cryptic binding sites for additional protein binding, enabling focal adhesion reinforcement. These processes can set a dimensional scale for cellular rigidity sensing.

SUMMARY

The present disclosure describes elastomeric surfaces comprising regions of heterogeneous rigidity at the micro- and nanoscale. The present disclosure also describes methods of making such surfaces, such as by exposing regions of an elastomeric film to an energy source, such as a focused electron beam (e-beam) or deep ultraviolet (UV) light, which can form patterned regions of micron or submicron spots, or both. The exposed regions can undergo a non-linear increase in rigidity as a function of the applied exposure (e.g., the electron dose or the UV dose). Cells cultured upon the surface can produce differential functional responses based on heterogeneous rigidity patterning on the surface, such as differential focal adhesion of the cells, differential cell differentiation of the cells; differential immune response; or differential growth of the cells. For example, human skeletal stem cells cultured upon surfaces patterned in this manner displayed differential focal adhesion co-localization to the rigid regions, a behavior that persisted as the area of the exposed regions was reduced to ~1 µm. On spots with diameters of ~250 nm and below, focal adhesion co-localization was lost. This implies that there exists a length scale for cellular rigidity sensing, with the critical length in the range of a few hundred nanometers.

In an example, the present disclosure describes an elastomeric substrate comprising a surface with regions of heterogeneous rigidity, wherein the regions are formed by exposing the elastomeric substrate to an energy source to form the regions such that the regions include a rigidity pattern comprising spots.

In another example, the present disclosure describes a method of culturing cells, the method comprising culturing cells upon a surface of an elastomeric substrate, the surface comprising regions of heterogeneous rigidity, wherein the regions are formed by exposing the elastomeric substrate to an energy source to form the regions such that the regions include a rigidity pattern comprising spots.

In another example, the present disclosure describes a method for fabricating a substrate, the method comprising forming a substrate of an elastomer, the substrate having a surface, and exposing selected regions of the surface to an energy source, the energy source configured to modify a rigidity of the selected regions.

BRIEF DESCRIPTION OF THE FIGURES

The file of this patent contains at least one drawing/photograph executed in color. Copies of this patent with color drawing(s)/photograph(s) will be provided by the Office upon request and payment of the necessary fee.

FIGS. 7A-7F show focal adhesion formation by mesenchymal stem cells on a PDMS surface having spots with the same rigidity, but with modulated spot diameter, with FIG. 7A showing a mesenchymal stem cell on spots having the largest relative spot diameter, and FIG. 7F showing a mesenchymal stem cell on spots having the smallest relative spot diameter.

FIGS. 8A-8F show the same mesenchymal stem cells as shown in FIGS. 7A-7F, respectively, but after paxillin staining of the mesenchymal stem cells, with FIG. 8A showing the paxillin staining of the mesenchymal stem cell on spots having the largest relative spot diameter, and FIG. 8F showing the paxillin staining on the mesenchymal stem cell on spots having the smallest relative spot diameter.

DETAILED DESCRIPTION

Figure 1A:
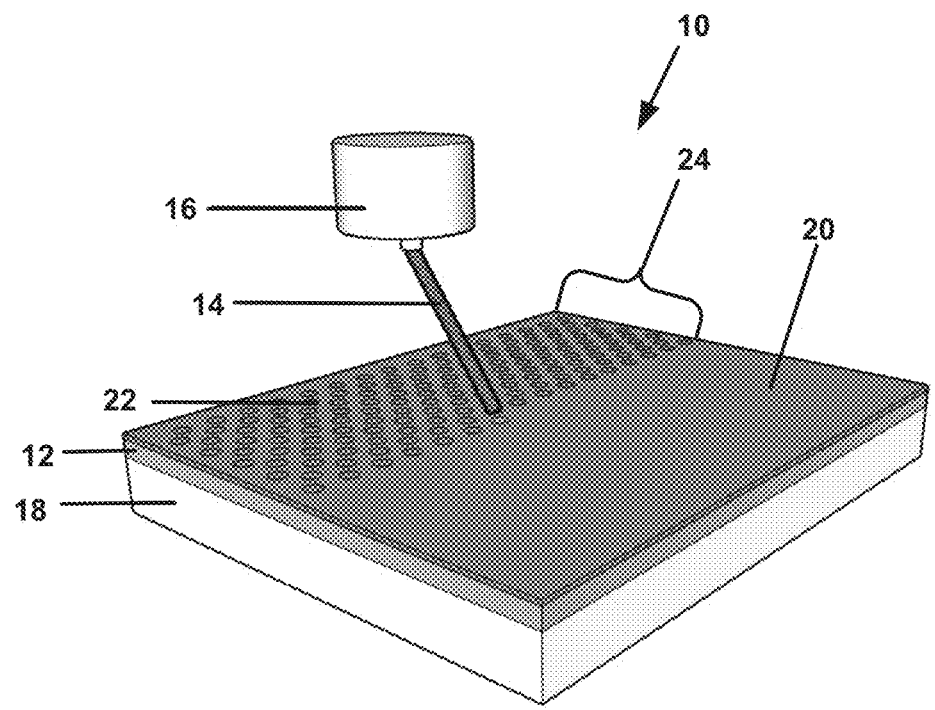
FIG. 1A shows a perspective view of a system for emitting an electron beam onto a poly(dimethylsiloxane) (PDMS) thin-film for selective modification of a stiffness of the PDMS film.

FIG. 1A shows a system 10 for selectively modifying a stiffness of an elastomer film 12 by exposing the elastomer film 12 to an energy source 14, such as an electron beam 14, from an energy source 16, such as an electron gun 16. In other examples, described in more detail below, the elastomer film 12 can be exposed to another energy source, such as deep ultraviolet light ("deep UV"). The elastomer film 12 can be deposited onto a substrate 18, such as a glass substrate 18, which can provide structural support to the thin elastomer film 12.

The elastomer film 12 can be configured to provide a support for living cell, wherein a heterogeneous rigidity pattern formed on an upper surface 20 of the elastomer film 12 can be configured to affect a characteristic of a living cell located on the upper surface 20 of the elastomer film 12. The heterogeneous rigidity pattern may be capable of producing a differential functional response in cells cultured on the elastomer based on heterogeneous rigidity patterning on the surface. The differential response can include, but is not limited to, at least one of differential focal adhesion of the cells, differential cell differentiation of the cells (such as T-cell or stem cell differentiation), differential immune response, or differential growth of the cells. For example, stem cells can show lineage-specific differentiation when cultured on substrates matching the stiffness corresponding to native tissue. Although tissues can be associated with Young's modulus values for bulk rigidity, at the sub-cellular level, and particularly at the micro- and nanoscales, tissues can be composed of heterogeneous distributions of particles, and fibers of varying rigidity. Skeletal stem cells can reside in a specialized biophysical and biochemical niche environment within the medullary cavity. The types of extra-cellular matrix architecture encountered by skeletal stem cells in vivo can range from a fibrillar scaffold of connective tissue to nanophase apatite crystals of mineralization. A skeletal stem cell can therefore encounter a composite environment of micro- and nanoscale topographical features and discrete rigidities, with elastic moduli ranging from 150 GPa (hydroxyapatite), to 5 GPa (collagen type I) or 2-7 kPa (plasma membrane). How cells sense and respond to the mechanical properties of their surroundings in a heterogeneous rigidity environment remains of interest. Other cells have been or are believed to respond to a heterogeneous rigidity pattern, such as the one formed on the elastomer film 12. Examples of cells that may respond to the heterogeneous pattern of the elastomer can include, but are not limited to, stem cells, cancer cells, nerve cells (such as neurons), bone cells (such as osteoblasts), and muscle cells.

The elastomer film 12 can comprise a material that is capable of being modified by exposure to the energy source 14, for example by becoming more rigid when exposed to the energy source 14. In an example, the elastomer film 12 can comprise poly(dimethylsiloxane) (PDMS), which is known to undergo additional crosslinking when exposed to certain energy sources 14, such as an electron beam 14 or deep UV. The elastomer film 12 can, therefore, be modified to present cells with surfaces having patterns with specific rigidities approximating the range of rigidities encountered in physiological environments. For example, elastomers, and PDMS in particular, can be used in cell adhesion or migration assays, or microfluidic and MEMS technologies due to its favorable optical, biocompatible and mechanical properties. The PDMS film 12 can be used to study the role of extracellular rigidity on cellular adhesion and differentiation due to the ease by which its rigidity may be precisely controlled by simply varying the base:accelerator ratio.

PDMS substrates can be patterned into spots or other micron-scaled structures, such as micron-scale pillars, that can facilitate the measurement of focal adhesion reinforcement and cellular forces in fibroblast cells. Because the rigidity can be dictated by a combination of the elastomer composition and the structure dimensions, e.g. diameter or height, or both, the pliable deformation of dimensionally defined structures by cellular forces can be precisely measured and used to generate real-time force maps across entire cells. One recognized shortcoming associated with elastomeric pillar structures is the introduction of topographical features to the cell assay system, a modulator of focal adhesion formation and cellular function. In order to understand in more detail how cell behavior can be dictated by the architecture of the extra-cellular matrix rigidity, it can be helpful to isolate the mechanical basis of rigidity-mediated mechanotransduction from that of topographical sensing.

Patterned structure arrays, such as pillar or spot arrays, can be formed by a lithography-generated molding process. For example, PDMS can be transparent to visible and ultraviolet light and therefore cannot, in general, be directly patterned by standard photolithography without the addition of a photoactive compound. However, PDMS can be sensitive to deep ultraviolet light (deep UV) and electron beam ("e-beam") irradiation, which can induce cross-linking of the elastomer. The cross-linking, in turn, can alter surface mechanical properties of the radiation-exposed elastomer.

The present disclosure shows that exposure of an elastomer, such as PDMS, to radiation, such as e-beam or deep UV exposure, can significantly alter the rigidity of the elastomer. This allows for the formation of two-dimensional elastomeric substrates with geometrically patterned heterogeneous rigidity. Exposed feature dimensions extended from the macroscale to the micron scale and to the nanoscale and covered a range of rigidities, which can be regulated by varying the applied dose of the radiation, e.g., the e-beam exposure dose or the deep UV exposure dose. As described in more detail below, a differential co-localization of focal adhesions to the patterned rigidity regions occurs with human skeletal stem cells, and this response can be maintained on micron and submicron sized regions. Further, it has been found by the inventors that cells can integrate the pattern of rigidity to which they are exposed by regulating the localization of focal adhesions formed in order to maintain their spread shape. This adaptation can occur across a range of feature stiffness and size. Rigid spots as small as 250 nm across can induce the formation of localized punctate focal adhesions, but this effect is not observed on patterned regions having a size of 100 nm across. These observations reveal the existence of a submicron machinery that may be used by cells to sense local rigidity. Knowing these geometrical limits can yield a better understanding of in vivo cell behavior in processes such as embryogenesis, wound healing and cellular metastasis. In addition, an understanding of the geometrical basis for rigidity sensing can be helpful for the design of implants with artificial smart surfaces allowing optimal interaction with cells in a tissue.

In an example, the elastomer film 12 can be a 120 µm-thick layer of PDMS that is deposited onto a glass substrate 18, such as by spin-coating PDMS onto the glass substrate 18. The glass substrate 18 can be treated with an oxygen plasma and coated with a final polymeric discharge layer 22, such as AquaSAVE, prior to exposure of the elastomer film 12 to the energy source 14.

The exposure of the energy source 14 onto the elastomer film 12 can be controlled so that only certain portions of the upper surface 20 of the elastomer film 12 are exposed to the energy source 14. For example, if the energy source 14 is a focused electron beam 14, as shown in FIG. 1A, the focused electron beam 14 can be scanned over the substrate surface 20 to create an array of defined spots 24. Alternatively, if the energy source 14 is a deep UV source 14, a mask (not shown) can be placed over the upper surface 20 of the elastomer film 12 with openings through the mask corresponding to the desired locations of the spots 24 in the array, wherein the openings allow the deep UV light to pass through the mask at the predetermined locations of the spots 24.

In an example, a PDMS mixture can be prepared at a 50:1 ratio of base PDMS polymer to accelerating agent. The PDMS mixture can be spin-coated onto a substrate 18, such as a glass substrate 18. The PDMS mixture can be cured for an extended period of time, such as at least about 1 hour, for example at least about 1.5 hours; 2 hours, 2.5 hours, 3 hours, 4 hours, 5 hours, 6 hours, 7 hours, 8 hours, 9 hours, 10 hours 11 hours, 12 hours, 18 hours, or 24 hours, and at a temperature sufficient to cure the PDMS, such as at least about 50° C., for example at least about 55° C., at least about 60° C., at least about 65° C., or at least about 70° C., to form an optically transparent viscoelastic elastomer film 12. The elastomer film 12 can be rendered hydrophilic by applying a short oxygen plasma treatment to facilitate a further spin-coating application of the electrically conducting layer 22, also referred to as a discharge layer 22, such as the polymer sold under the trade name AquaSAVE by Mitsubishi Rayon America, Inc., of New York, N.Y., USA, to suppress charging during e-beam exposure.

In an example, the rigidity pattern of the elastomer film 12 can be generated in the elastomer with e-beam exposure doses ranging from about 500 microcoulombs per square centimeter ($\mu C/cm^2$) to about 4,000 $\mu C/cm^2$. The electron beam 14 can be formed using an accelerating voltage of about 30 kilovolts (kV) and a beam current of about 2.5 nanoamperes (nA).

Figure 1B:
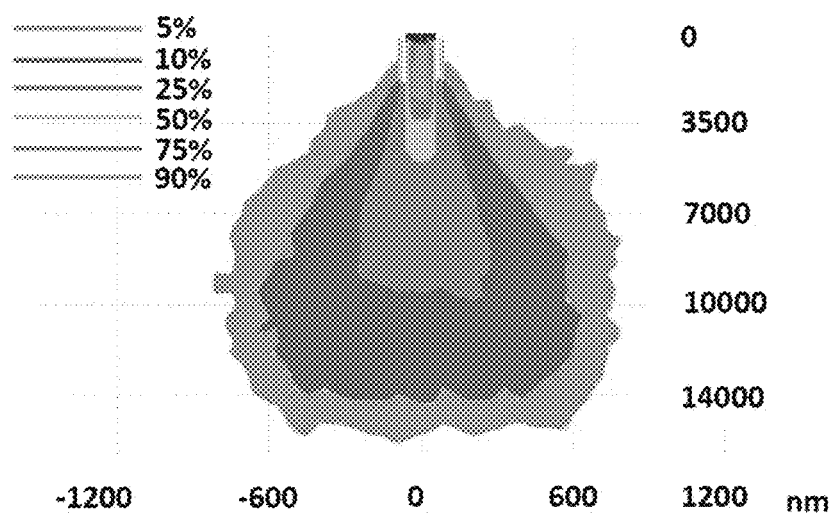
FIGS. 1B and 1C show electron trajectory and scattering within a PDMS film, as determined by Monte Carlo simulations of exposure of PDMS to electron beams.
Figure 1C:
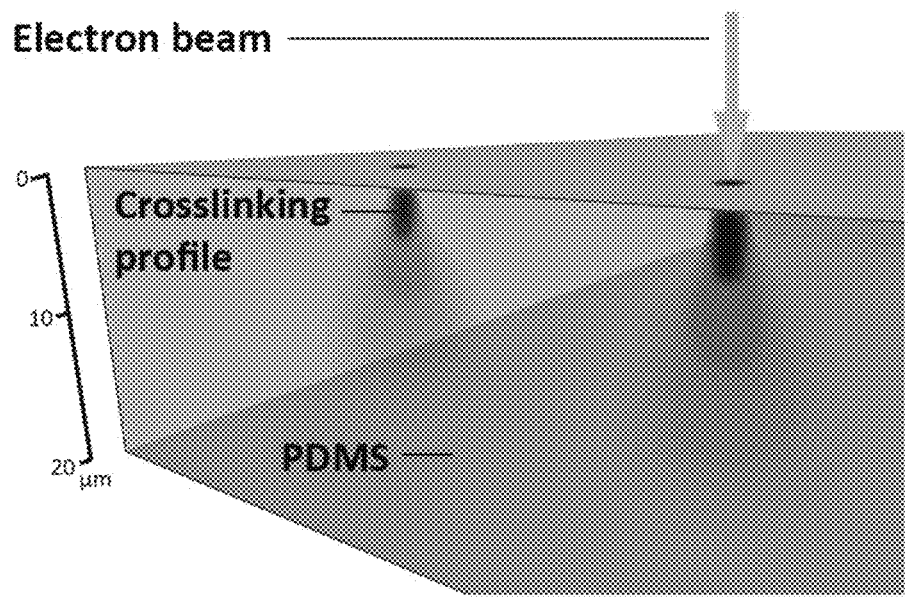

In the case of an electron beam 14, the absorbed electron energy within the PDMS film 12 can be determined by two factors: (i) the incident electron energy (such as about 30 kilo electron volts (keV)); and (ii) the scattering of electrons within the elastomer, which can depend on the density of the elastomer. Monte Carlo simulation analysis was conducted to determine the expected scattering of electrons in the electron beam 14. The Monte Carlo simulation indicated that the penetration depth exceeded about 15 micrometer (µm), but that over 90% of the e-beam energy was absorbed within approximately the top 3 micrometer (µm) of the elastomer, as shown in FIG. 1B. As shown in FIG. 1C, the penetration into PDMS can result in a scattering profile having a columnar shape with a broad spreading base that diminishes in intensity with increasing depth, e.g., a general conical profile of the elastomer crosslinking. Lateral scattering within the top layer was found to be confined to about 30 nanometers (nm) at 30 keV.

Figure 1D:
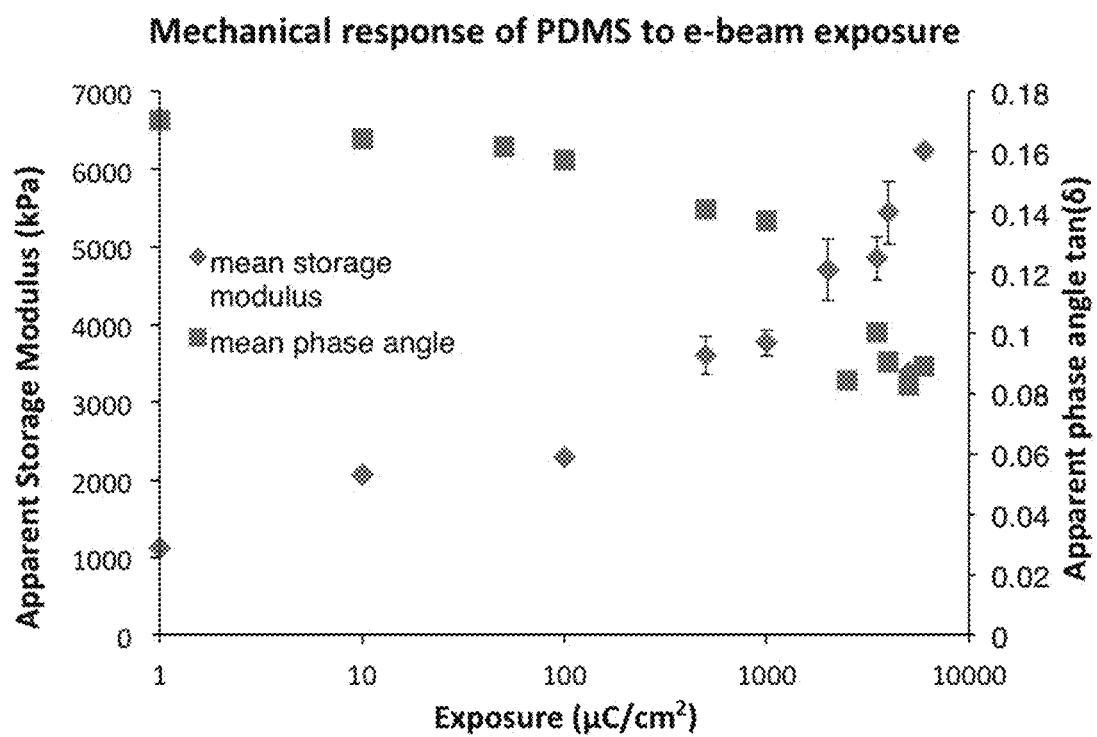
FIG. 1D is a graph of the relationship between stiffness (e.g., modulus) as a function of electron beam exposure
Figure 1E:
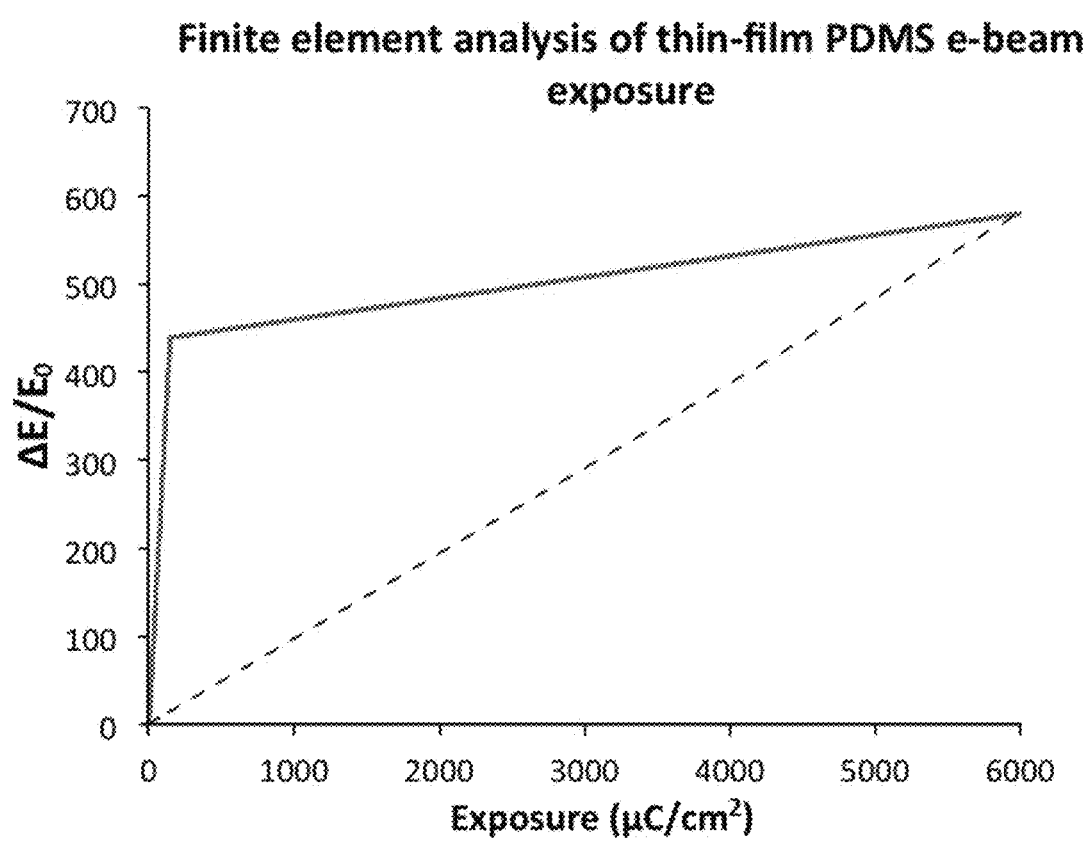
FIG. 1E shows a graph of a function relating Young's modulus changes due to the e-beam exposure as a function of $E/E_0$ where E is the modulus of the 3 µm PDMS film and $E_0$ is the modulus of a 120 µm spin-coated film.

Nanoindentation can be employed to characterize the change in the elastic properties of the elastomer as a function of exposure to the energy source 14. In an example, measurements can be made on large area exposures, such as at least about 1 square millimeter ($mm^2$), for exposure doses up to about 6,000 $\mu C/cm^2$. In an example, a diamond flat-punch indenter tip of radius 76.4 µm was oscillated at a frequency of 110 Hz as the nanoindenter head approached the sample. After contact with the elastomer surface, the nanoindenter head can maintain a constant load and deflect the springs 1.5 µm. The tip can remain in contact with the elastomer, oscillating about 500 nm, while recording the amplitude and phase of the force and displacement of the embedded tip. As mentioned above, the Monte Carlo simulation indicated that most of the electron energy is deposited in about a 3 µm thick layer at the surface of the elastomer film 12. In order to extract the mechanical properties of this layer from the force-displacement curves, finite element analysis (FEA) can be applied to model a multilayer stack including the exposed layer, the elastomer film 12 and the underlying substrate 18. The FEA calculations can also take into account the prestrain induced in the elastomer as a result of the spin coating process and the contraction of the elastomer as a result of the cross-linking due to exposure to the energy source 14. The FEA calculations can be determined from depth profiles of the exposed features (as shown in FIGS. 2A-2D) and nanoindentation measurements on unexposed elastomer films (such as a 10 mm-thick PDMS block used as a reference). The results of the nanoindentation and FEA curve-fitting, in terms of the relative increase in Young's modulus for the top 3 μm of the elastomer film 12, are shown in FIG. 1D, indicating that exposure to the energy source 14 can cause an increase in the stiffness of the polymer, such as up to two orders of magnitude or more. FIG. 1D shows that e-beam exposure of a PDMS film can cause an increase in stiffness of the polymer due to crosslinking and also a reduction in volume leading to increased pre-strain in the film. The increase in Young's modulus can be bounded by the unexposed material properties and the expected level of pre-strain due to e-beam exposure. FIG. 1D shows the resulting apparent $\mu_{storage}$ and tan (δ) as a function of e-beam dose.

Figure 2A:
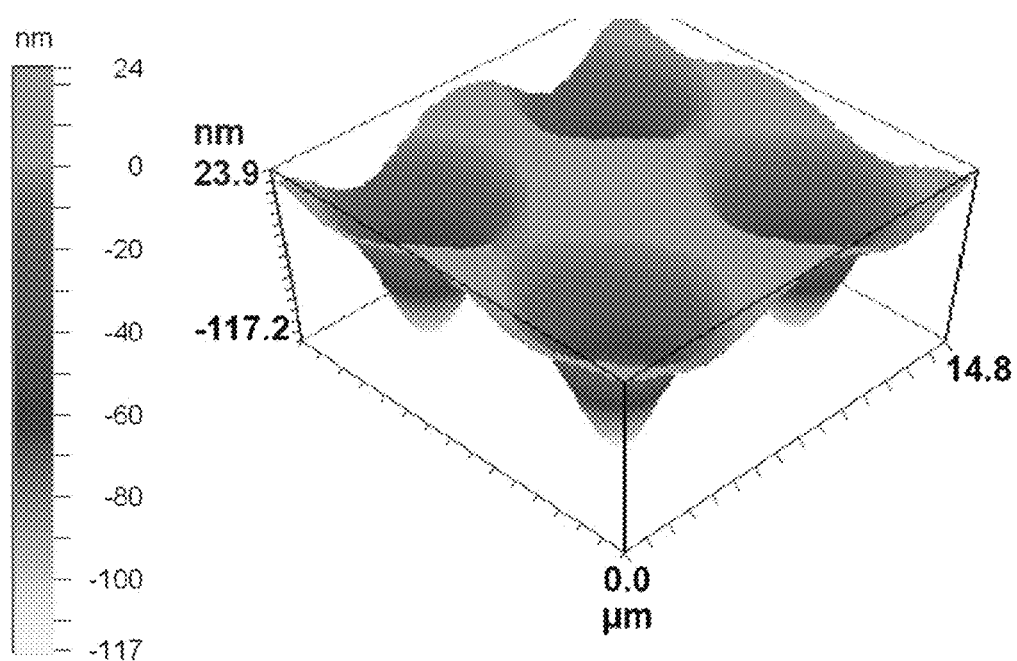
FIGS. 2A and 2B show the physicochemical modulation of PDMS substrates by focused electron-beam patterning.
Figure 2B:
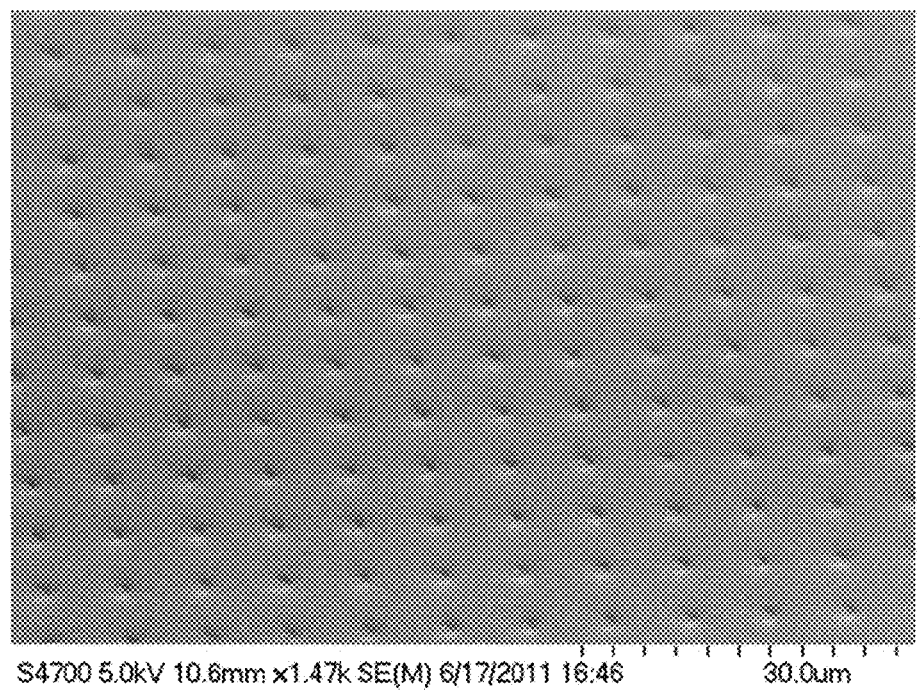
Figure 2C:
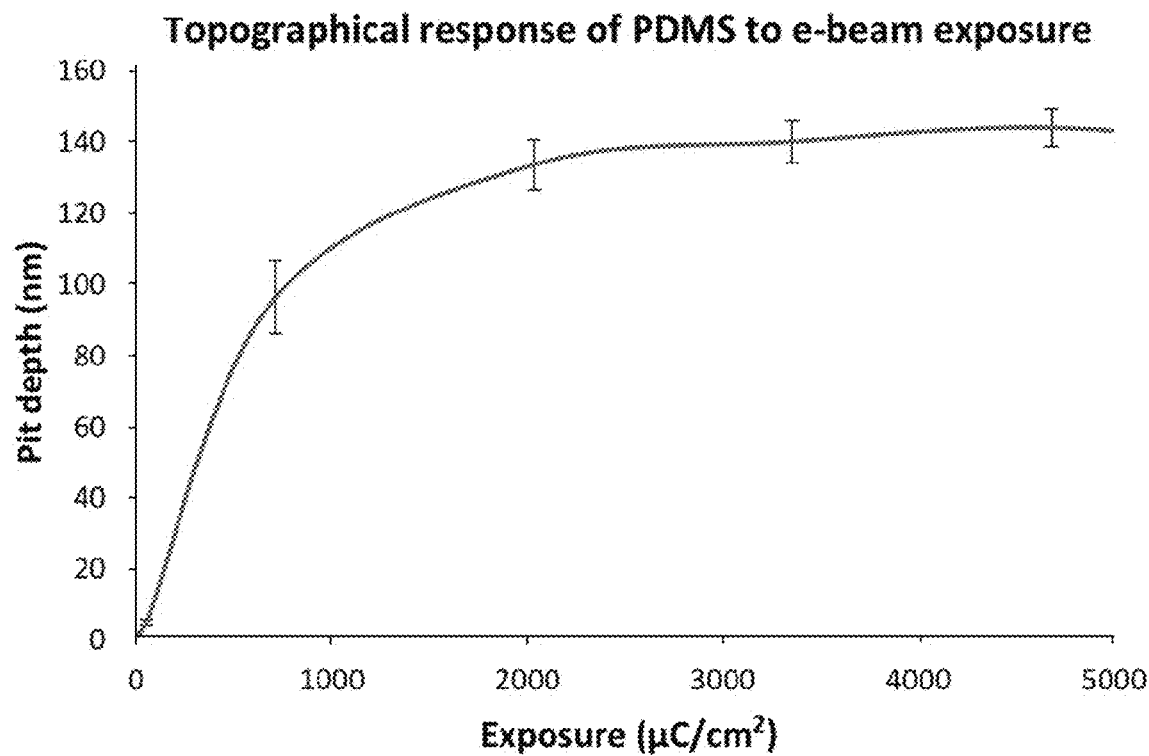
FIG. 2C shows a graph of the depth of pits in the elastomer as a function of electron beam dose.

The application of the energy source 14 to the elastomer can result in the formation of shallow depressions surrounding the exposed regions. Without being bound to any theory, the inventors believe that this can be attributed to minor contraction of the elastomer as a result of the exposure-induced cross-linking, which can cause circumferential stressing beyond the periphery of the exposed region (see FIG. 2A and FIG. 2B). E-beam exposure doses of 4,000 μC/cm$^2$ initiate nanoscale contractions of PDMS resulting in an undulating topography of shallow pits, as shown in FIGS. 2A and 2B. This topographical response can be dose dependent. As shown in FIG. 2C, low doses of 50 μC/cm$^2$ resulted in undulations of approximately 4 nm depth. PDMS contraction and pit depth was observed to plateau with doses of 2,200 μC/cm$^2$, and resulting pits measured about 140 nm in depth.

Figure 2E:
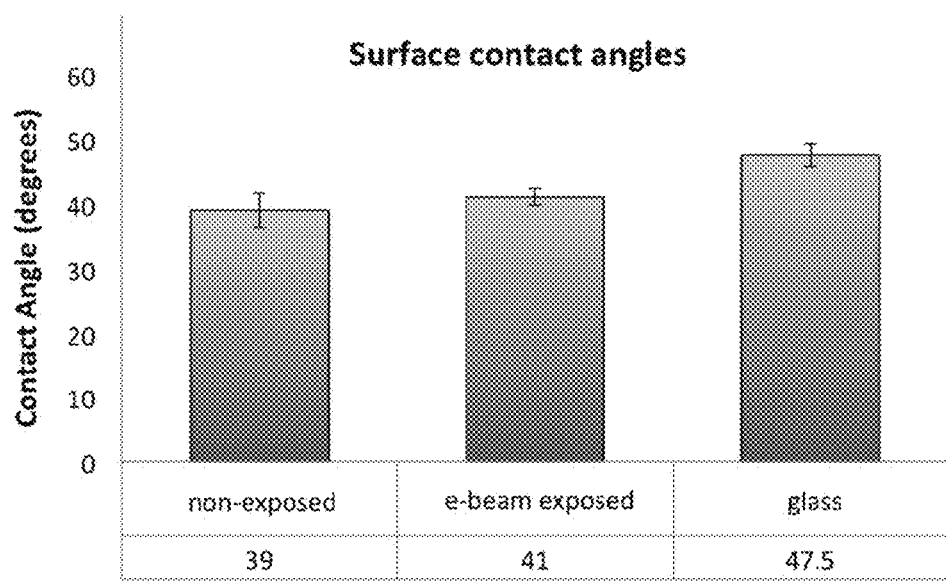
FIG. 2E shows a chart of the surface water contact angle of the PDMS both before and after electron beam exposure as well as the contact angle for glass.
Figure 2D:
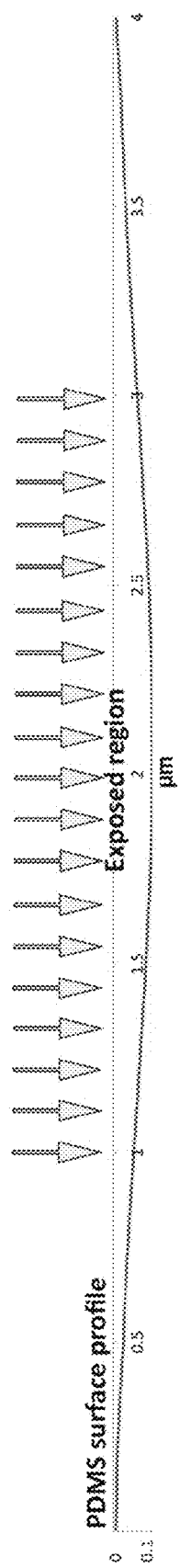
FIG. 2D shows a surface topography of a region of PDMS exposed to an electron beam.

Although nanoscale pits have been found to reduce focal adhesion reinforcement when greater than 73 nm in depth, these effects can be negated when pit diameters are within the micron range and the feature radius of curvature is below about 200 nm (see FIG. 2D). FIG. 2D shows the surface topography of PDMS after exposure to an electron beam, as determined by profilometry of the surface. Profilometry revealed that doses of up to 10,000 μC/cm$^2$ did not increase the pit depth. The resultant topography was composed of smooth undulating pits with a radius of curvature of approximately 20 μm. In order to isolate the possible involvement of the topographical modulation on cellular function, e.g., the topography arising from e-beam mediated elastomer contraction, on cellular function, control elastomer substrates were fabricated by imprinting with a negative elastomer shim to yield topographically yet non-rigidity modified elastomer substrates. Cellular response to these control substrates are described below in the Example.

Samples were cleared of aquaSAVE prior to physicomechanical analysis and the chemical effects of e-beam irradiation on the elastomer were assessed prior to in vitro cell experiments to ensure that the modulation of cellular function was exclusively rigidity dependent and not as a result of altered surface hydrophobicity or protein adsorption, or both. According to oxygen plasma surface wettability analysis, the wettability of experimental elastomer substrates was analyzed by contact angle measurements (see FIG. 2E), which confirmed no significant differences in water contact angle between all the materials that form the cellular support (e.g., PDMS and glass). X-ray photoelectron spectroscopy (XPS) analysis, however, indicated a significant reduction in the surface carbon profile of the elastomer when irradiated with an intermediate area dose. At a dose of about 1,000 μC/cm$^2$ the surface carbon content decreased by about 50% (see FIG. 2F).

In order to assess the protein and cellular response to heterogeneously patterned rigidities, elastomer substrates were patterned with an array of spots with diameters ranging from about 100 nm to about 2 μm and an edge-edge spacing of about 3 spot diameters and with the doses indicated previously. The inter-spot distance was modulated proportionally with spot diameter in order to ensure that the cells were exposed to a relatively constant ratio of higher rigidity and lower rigidity.

The protein adsorption distribution can be assessed by analyzing the fluorescence intensity profile of labeled fibronectin vs. the bright field differential interference contrast (DIC) intensity on the e-beam exposed materials and was analyzed with ImageJ. The bright field intensity increased sharply at the irradiated regions, demonstrating that e-beam exposed elastomer can cause minimal lateral scattering during irradiation and indicating the presence of diffractive modification. On the other hand, the fluorescence intensity profile was unchanged at the sites of e-beam exposure, indicating a uniform distribution of protein adsorption on the patterned substrates (FIG. 2G).

Effect of Elastomer Rigidity on Focal Adhesion Formation

The effect of spot rigidity on the formation of focal adhesions was investigated. Elastomer substrates were formed and exposed to e-beam radiation of varying doses in order to form spots having varying rigidities (shown in FIGS. 3A-3F). The spots of each elastomer substrate shown in FIGS. 3A-3F had the same spot diameter of about 2 μm. The elastomer substrates were sterilized in 70% ethanol and washed in phosphate-buffered saline solution (PBS) before seeding of immortalized human mesenchymal stem cells (hMSCs) derived from human bone marrow aspirates and stably transduced by a retroviral vector containing the gene for the catalytic subunit of human telomerase (hTERT). The hMSCs were cultured on experimental elastomer substrates (e.g., substrates where the spots had been exposed to e-beam radiation) and control substrates (e.g., unexposed substrates) for about 18 hours before fixing and preparing for immunocytochemistry. The hMSCs were stained for the focal adhesion protein paxillin (FIGS. 4A-4F), and analysis of focal adhesion co-localization and intensity on the irradiated regions was performed with ImageJ image processing software.

Analysis of focal adhesion formation on exposed spot regions showed that focal adhesion co-localization to the exposed regions increased with applied electron beam dose. On substrates patterned with 4,000 μC/cm$^2$ and spots measuring 2 μm in diameter, MSCs formed punctate focal adhesions that co-localized significantly with the underlying exposed region. This effect was observed to diminish with decreasing spot dose (FIGS. 3A-3F, FIGS. 4A-4F, and FIG. 5). It has been found that increased focal adhesion colocalization appears to increase to approximately 60% focal adhesion colocalization at a dose of at least 4000 μC/cm$^2$. Cellular spreading or actin cytoskeleton organization does not appear to have affected MSCs cultured on 2 μm diameter spots of modulated rigidity (see FIGS. 3A-3F). However, paxillin staining (FIGS. 4A-4F) revealed a significant increase in focal adhesion colocalization and fluorescence intensity with increasing spot stiffness.

Figure 6:
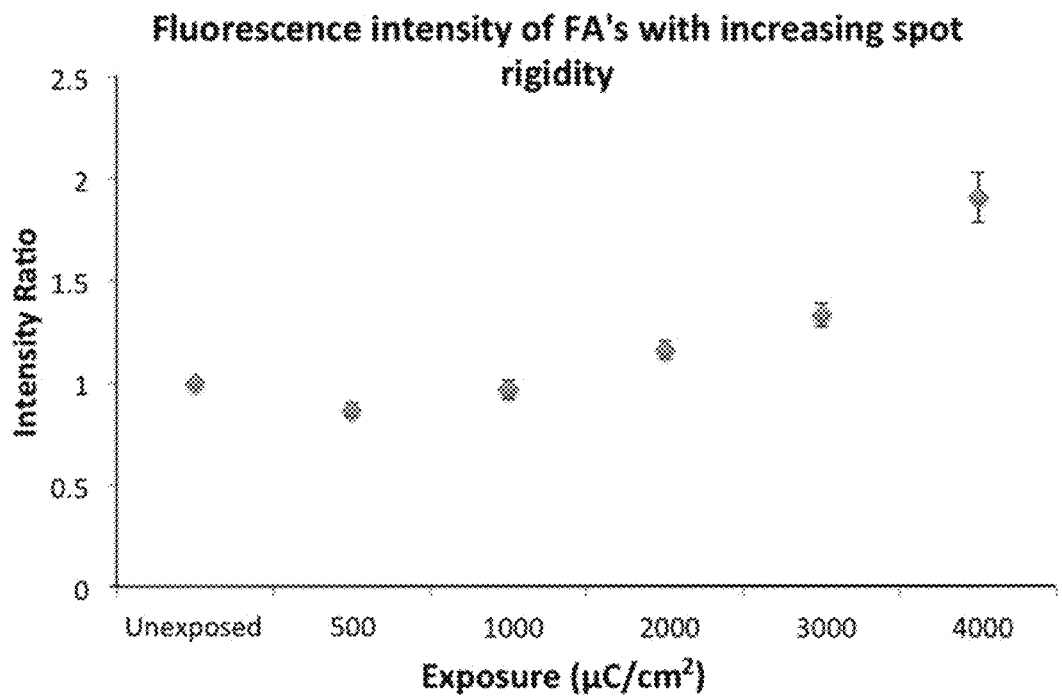
FIG. 6 shows a graph of the fluorescence intensity of focal adhesions associated paxillin as a function of electron beam exposure dose which in turn shows the relationship between colocalization and spot rigidity.
Figure 9:
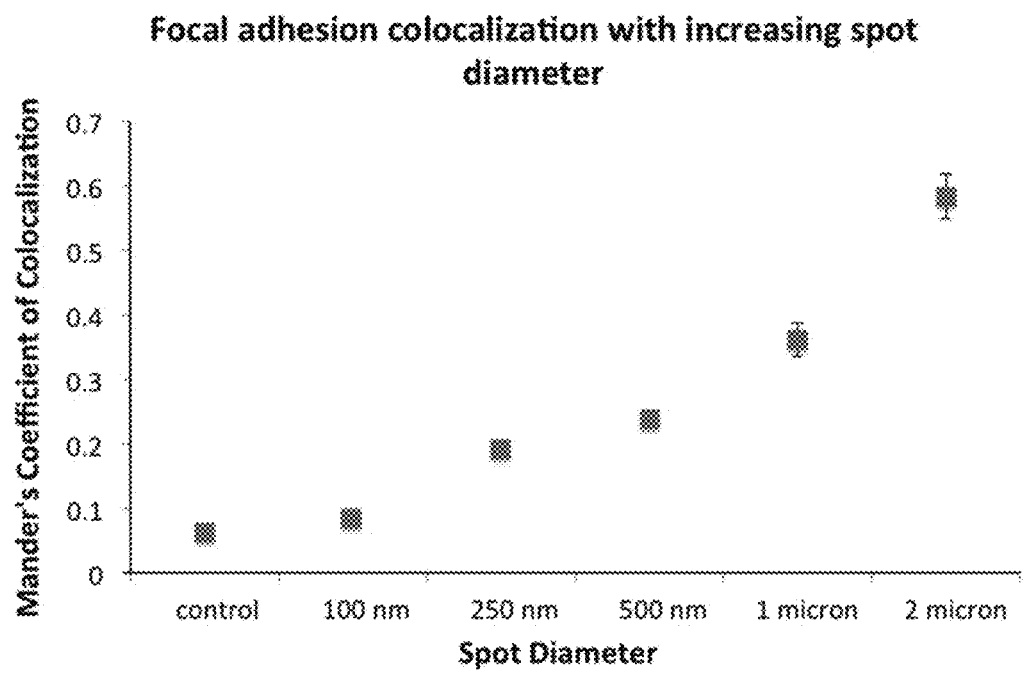
FIG. 9 shows a graph of Mander's coefficient of colocalization as a function of spot diameter.

On spots having lower rigidity (e.g., less e-beam dosage), elongated focal adhesions were observed to initiate at the irradiated regions yet extended onto the unexposed inter-spot regions, also referred to as "soft" regions, and co-localization was eliminated with decreasing rigidity. Interestingly, fluorescence intensity of focal adhesion associated paxillin was also significantly increased on stiff regions (FIG. 6) indicating increased recruitment of paxillin to focal adhesions formed on the stiffer elastomer regions. Varying the spot rigidity was also observed to significantly modulate total focal adhesion area, but not cellular spreading.

Effect of Rigid Area Size on Focal Adhesion Formation

The effect of the size of rigid areas of elastomer substrates was also investigated. Elastomer substrates were formed and exposed to e-beam radiation of the same dose, but the diameter of the spots that this dose was applied to was varied resulting in rigid regions having varying spot diameters (shown in FIGS. 7A-7F). The spots of each elastomer substrate shown in FIGS. 7A-7F were exposed to the same e-beam dose of 4000 $\mu C/cm^2$. Analysis of focal adhesion co-localization to the rigid spots in the substrates of FIGS. 7A-7F revealed that punctate focal adhesion co-localization was dependent on spot size. Reducing the exposed spot diameter from 2 µm to 100 nm significantly decreased focal adhesion co-localization (FIGS. 7A-7F, FIGS. 8A-8F, and FIG. 9). Cellular spreading or actin cytoskeleton organization does not appear to have affected mesenchymal stem cells cultured on spots exposed to electron beams having a dose of 4000 $\mu C/cm^2$, and with varying spot diameter (see FIGS. 7A-7F). However, paxillin staining (FIGS. 8A-8F) revealed a significant increase in focal adhesion colocalization and fluorescence intensity with increasing spot diameter.

Figure 10:
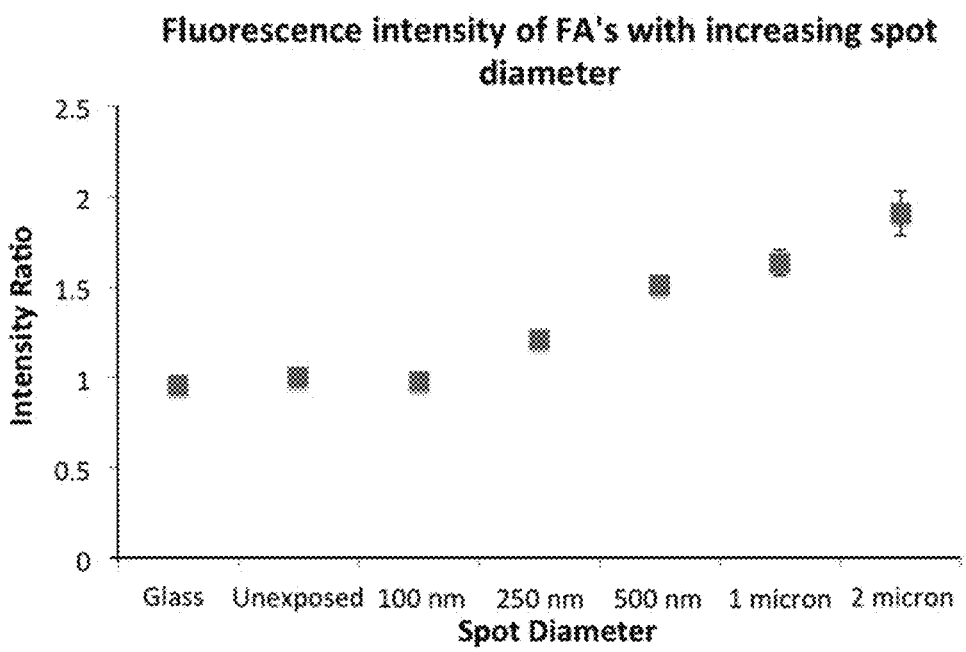
FIG. 10 shows a graph of the fluorescence intensity of focal adhesions associated paxillin as a function of spot diameter.

By decreasing the spot diameter and inter-spot spacing, colocalized, punctate focal adhesions became less frequent. Rather, focal adhesions were observed to bridge between multiple spots. Interestingly, focal adhesions that bridged between multiple spots were associated with punctate domains of increased paxillin fluorescence intensity which were shown to occur at the irradiated regions (FIG. 10), indicating focal adhesion sensing machinery can initiate discrete protein reinforcement along the focal adhesion plaque. Varying the spot diameter was observed to significantly modulate total focal adhesion area, yet not cellular spreading. However, varying the spot size was observed to affect cellular motility. Specifically, cell velocity and mean migration distance were significantly reduced on substrates patterned with dots >500 nm in diameter.

As noted above, deep ultraviolet light ("deep UV") can also be used as the energy source 14 that can trigger cross-linking within the elastomer film 12 in order to modify the stiffness of the elastomer. The term "deep ultraviolet light' or "deep UV," as used herein, can refer to ultraviolet light having a wavelength of less than about 300 nanometers and greater than about 150 nanometers, such as from about 190 nanometers to about 260 nanometers. In some examples, UV light having a wavelength of about 248 nanometers can be used, and in other examples UV light having a wavelength of about 193 nanometers can be used. The deep UV light can be patterned onto the elastomer film 12 using, for example, a mask that allows passage of deep UV light onto some areas of the elastomer film 12, e.g., to form the array of spots 24, and blocks passage of the deep UV light from reaching other areas of the elastomer film 12, e.g., the areas between the spots 24.

In an example, the modification in rigidity of the elastomer film 1 the modified stiffness of the spots 24, can be achieved without requiring different dimensions or sizes of structures at the upper surface 20 of the elastomer film 12. Previously, micro- or nano-scale structures, such as nanoscale pillars have been used to modulate the rigidities of the substrate, where the size, shape, and/or dimensions of the pillars have been modified in different regions to provide for different rigidities at the different regions. In contrast, the elastomer films 12 described herein and the methods described herein for making them have been found to provide for different rigidities within the elastomer, e.g., PDMS, without having to modify micro- or nano-scale structures, such as pillars. In other words, the methods described herein can provide for modification of the rigidity of the material itself, and not on the macro-level rigidity that can be provided to the material by physical characteristics of micro- or nano-scale structures made up of the material. The technique described herein (e.g., a selective increase of elastomer rigidity in a lithographically patterned fashion) can also be used on elastomeric surfaces that have been molded into three-dimensional structures such as pillars. The result would be pillared surfaces with locally variable stiffness.

Discussion

Integrin mediated adhesions play dual physiological functions—as physical structures that direct and regulate tissue and organ morphogenesis, and as bi-directional mechanosensors that modulate cellular signaling events. Cells can be very sensitive to the physical state of the local environment. Matrix rigidity can be conveyed through macromolecular focal adhesions in a bidirectional manner, modulating cellular function and focal adhesion morphology. Stiffer matrices can generate larger focal adhesions through increased intracellular tension, and study of bulk systems of rigidity indicates that cells respond to rigidity gradients, and migrate from regions of lower to higher rigidity, in a process termed durotaxis.

Major differences in focal adhesion reinforcement and density are observed in cells cultured on surfaces with bulk compliance (sub-kPa to a few kPa), relative to cells cultured on surfaces with bulk rigidity (hundreds of kPa to a few MPa). However, conflicting hypotheses exist on the mechanisms of bulk-rigidity mediated changes to focal adhesion reinforcement and subsequent cell function. Cells can exert a mechanical force on individual fibers of the matrix and gauge the feedback to make cell-fate decisions. By increasing the density of binding sites within a system, the number of individual sites available for focal adhesion formation is also increased. This contrasts with data indicating that altered rigidity can induce changes to cellular function irrespective of binding site density.

In an example, direct write e-beam patterning can be used to produce geometrical patterns of increased rigidity on viscoelastic elastomer films 12, such as PDMS substrates. By controlling the size of spots in the micrometer and submicrometer range, for example from about 2 µm to about 100 nm, and an edge-to-edge distance (e.g., the distance between adjacent spots) of about 6 µm to about 300 nm, a substrata with defined distributions of heterogeneously increased rigidity can be reliably created with dimensions ranging from the micro to the nanoscale. Furthermore, this observable increase in substrate rigidity was not associated with modulations in binding site density or polymer concentration.

To study the effects of discrete spatial rigidity on focal adhesion formation and cell morphology, the effects of substrate rigidity can be isolated from the influences of substrate topography and chemistry, which have been shown previously to modulate the reinforcement of focal adhesions, dynamic turnover of focal adhesion associated proteins, and integrin mediated signaling activity.

As mentioned above, minor topographical modification, such as via the contraction of the elastomer as a result of cross-linking induced by exposure to the energy source, such as an electron beam, was observed for all doses. Shallow depressions were observed with increasing exposure. These features had depths which plateaued at 120 nm and diameters which extended to a maximum of twice the original exposed dot diameter. These depressions had a radius of curvature of approx. 20 μm and a feature height:radius of curvature ratio of approx. 1:200. Importantly, cellular studies into nanoscale feature curvature have revealed a critical feature height:radius of curvature ratio of 1:1, and that substrates possessing nanofeatures with radius of curvatures greater than this do not initiate contact guidance or modulate focal adhesion formation. In order to verify that the minor topographical undulations produced by e-beam exposure indeed did not influence focal adhesion formation, we fabricated control "topography" substrates from inverse replica shims. Cells plated on control substrates displayed no response to the topography and no focal adhesion co-localization to patterned features as was seen on the e-beam exposed substrates (FIGS. 3A-3F).

Figure 2F:
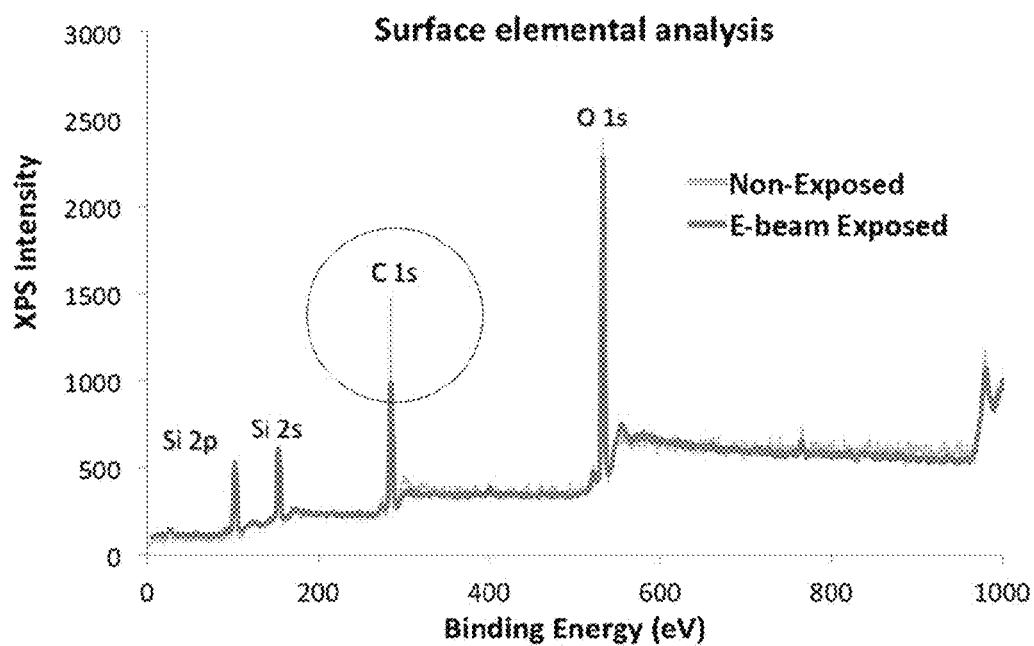
FIG. 2F shows an X-ray photoelectron spectroscopy analysis of a PDMS surface both before and after electron beam exposure.
Figure 2G:
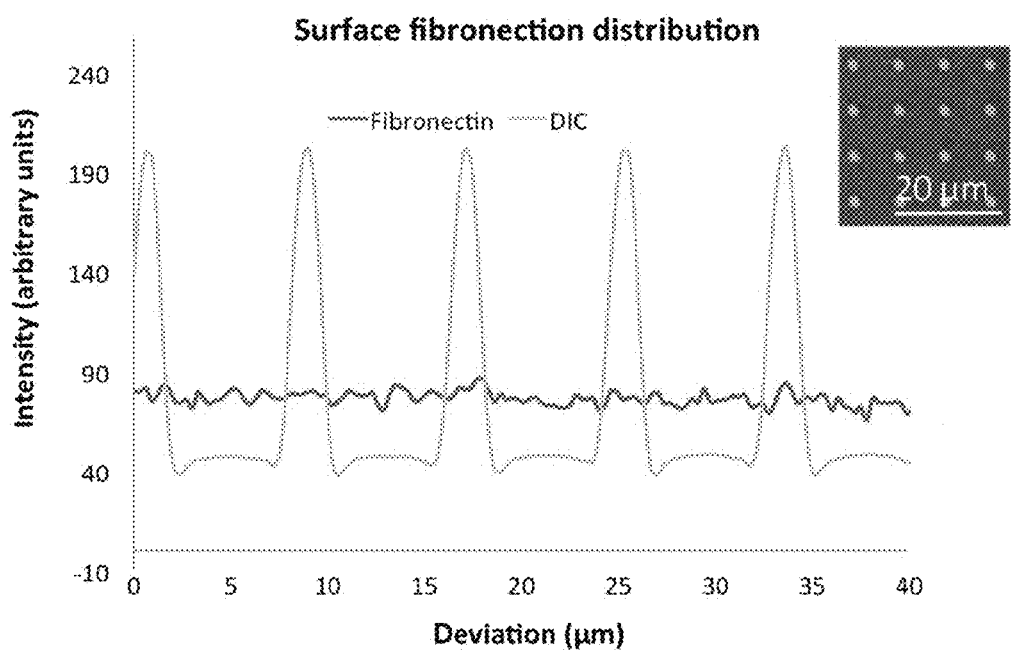
FIG. 2G shows a graph of the surface fibronectin distribution of PDMS after electron beam exposure.
Figures 3A, 3B, 3C, 3D, 3E, 3F:
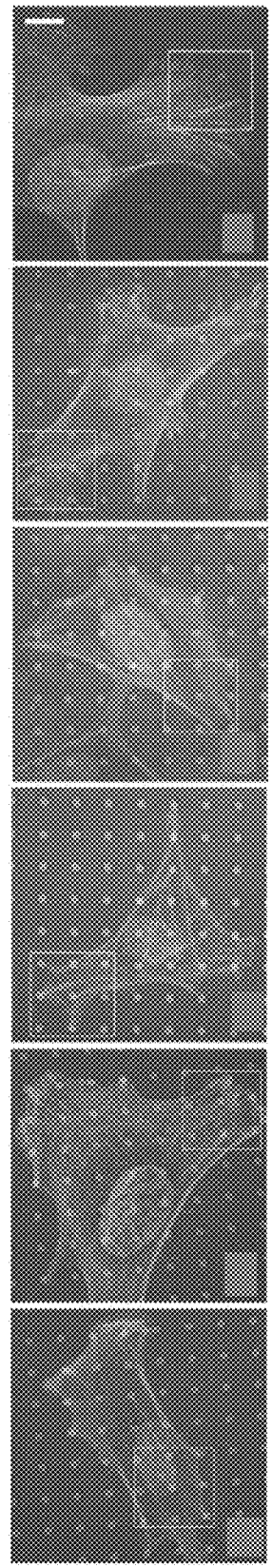
FIGS. 3A-3F show focal adhesion formation by mesenchymal stem cells on a PDMS surface having 2 μm spots with modulated rigidity, with FIG. 3A showing a mesenchymal stem cell on spots having the highest relative rigidity, and FIG. 3F showing a mesenchymal stem cell on spots having the lowest relative rigidity.
Figures 4A, 4B, 4C, 4D, 4E, 4F:
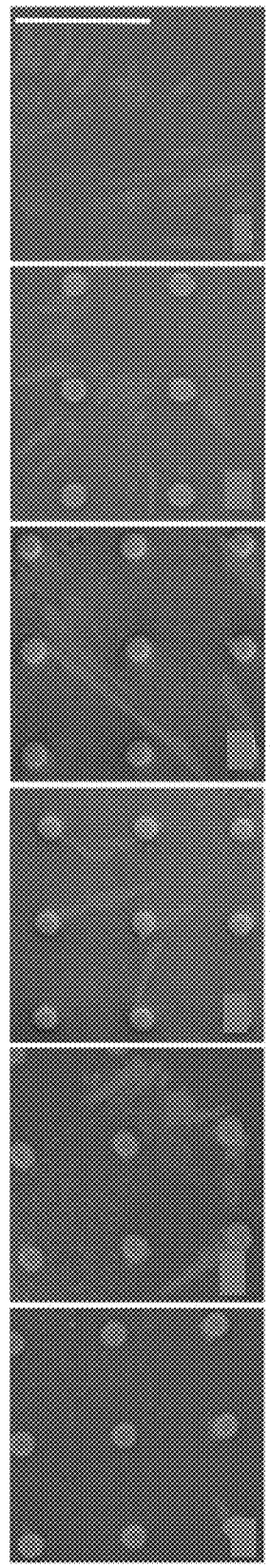
FIGS. 4A-4F show the same mesenchymal stem cells as shown in FIGS. 3A-3F, respectively, but after paxillin staining of the mesenchymal stem cells, with FIG. 4A showing the paxillin staining of the mesenchymal stem cell on spots having the highest relative rigidity, and FIG. 4F showing the paxillin staining on the mesenchymal stem cell on spots having the lowest relative rigidity.
Figure 5:
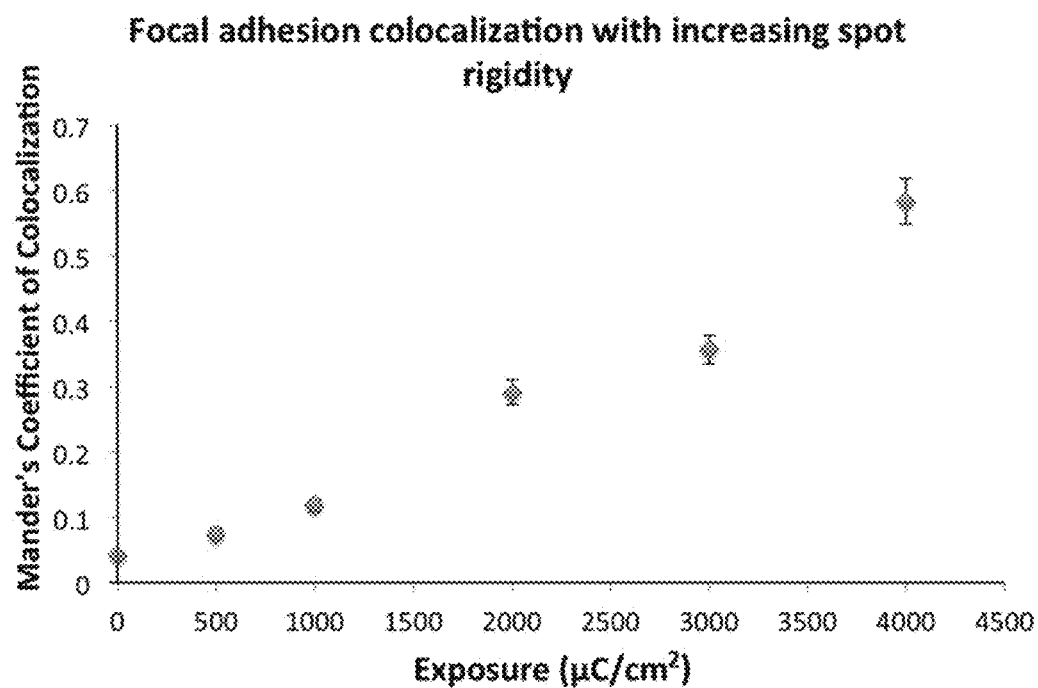
FIG. 5 shows a graph of Mander's coefficient of colocalization as a function of electron beam exposure dose, which in turn shows the relationship between colocalization and spot rigidity.

We note that, in contrast, some aspects if the PDMS surface chemistry can be affected by focused e-beam exposure, such as a reduction in the measured surface carbon content (FIG. 2F). This was also present in other observations that described a similar reduction in carbon content in PDMS following exposure to UV light. Here the PDMS underwent a silica-like chemical transformation accompanied by an appropriate change in the bulk PDMS refractive index. Without wishing to be bound by any theories, the inventors speculate that similar e-beam induced changes in PDMS refractive index, greatly aided in the bright field imaging of the exposed rigidity pattern, which, in fact, aided microscopy-based co-localization analysis.

PDMS hydrophobicity can promote rapid non-specific protein adsorption due to inherent charges present along the protein molecule. Oxygen plasma was employed to enhance PDMS wettability and enable the application of a water-soluble electrical discharge layer to enable e-beam patterning. The plasma treatment can also aide in reducing substrate hydrophobicity as indicated by contact angle analysis and reported previously. As noted above (and shown in FIG. 2G), differential fibronectin adsorption on heterogeneous rigidity substrates was not observed, and it is therefore believed that the observed focal adhesion co-localization effects cannot be attributed to differences in protein adsorption between the irradiated and non-irradiated regions.

Focal adhesion reinforcement and induction of actin organization require certain threshold densities of adhesion ligands. However, the existence of a minimum length scale at which cells can sense rigidity is of interest. The results described herein demonstrate that the formation of focal adhesions in mesenchymal stem cells cultured on substrates with heterogeneous rigidity is dependent both on feature stiffness and size. The formation of discrete punctate focal adhesions coupled with an increase in paxillin recruitment on spots ≥1 μm in diameter, indicate that this length scale lies between 500 nm and 1 μm. Paxillin recruitment to focal adhesions and subsequent phosphorolation can be essential for high focal adhesion traction over a broad range of ECM rigidities.

Additionally, a reduction in cell motility was observed when the cells were cultured on stiff regions of increasing diameter. This observation differs significantly from durotaxis observations with bulk rigidities where increased cellular motility is observed with increasing substrate stiffness. Similarly, other observations showed significant increases in cell motility when cultured on spots of clustered adhesion ligand. This seems to imply that the cellular response to adhesion ligand density and subsequent and focal adhesion formation is mediated via independent mechanistic processes to those that govern focal adhesion reinforcement on regions of increased rigidity.

We also observed that on spots ≤1 μm in diameter, focal adhesions had a tendency to extend paxillin domains, and single focal adhesions were associated with multiple rigid spots. The results described herein suggest that rigidity mediated adhesion can be regulated by the same machinery that governs focal adhesion assembly and reinforcement and that this machinery can be capable of recognizing localized discrepancies in matrix rigidity.

Tissues do not represent bulk rigidity systems, but rather can be composed of heterogeneous distributions of particles, and fibres of varying rigidity. We have developed a new type of biomimetic surface comprising regions of heterogeneous rigidity on the micro- and nanoscale by writing on PDMS films with an electron beam. Finite element analysis of nanoindentation measurements on these surfaces reveal a substantial increase in the Young's modulus of the elastomer as a result of the e-beam exposure. In a semi-planar system, the cellular rigidity sensing apparatus can be capable of sensing discrete submicron discrepancies in the matrix rigidity, and that focal adhesions demonstrate intrinsic "local" reinforcement in response to rigid features measuring ≥500 nm in diameter.

Different cell types can respond differently to rigidity and can have different spatial and rigidity requirements to elicit particular behaviors and responses. The versatility of the patterning system presented here can be applied to a broad range of cellular systems in order to elucidate the specific requirements for each. Understanding these requirements can be used to guide the design of new types of tissue scaffolds and can have implications in the treatment of cancer and other diseases.

EXAMPLE

Other aspects and advantages of the present invention will be understood upon consideration of the following illustrative example.

Substrate Fabrication

Microscope cover-glasses (Corning, NJ, USA) (2.2 mm2 No. 0) were cleaned for 12 h in a 1% v/v solution of the detergent MICRO-90 (International Products, NJ, USA), rinsed in reverse osmosis water ($ROH_2O$) and blown-dry in a stream of filtered nitrogen. Sylgard 184 PDMS (Dow Corning, MI, USA) was mixed with the supplied accelerating agent at a ratio of 50:1 for 5 min and degassed under vacuum for 10 minutes at 5 Torr. PDMS (0.5 ml) was applied to the microscope cover-glasses and spin-coated for 45 s at 1000 r.p.m. and an acceleration of 400 r.p.m. $s^{-1}$ to form a uniform film. The PDMS-coated cover-glasses were cured for 17 h at 70° C. before further processing. Substrates were subjected to an oxygen plasma in a tabletop Carrick PDC32G plasma cleaner for 10 seconds at a RF power of 18 W to induce surface hydrophilicity. Samples were next coated with a conductive discharge layer to facilitate e-beam exposure. A 5 nm thick discharge layer was applied to the substrates by spin coating 100 ul of AquaSAVE (Rayon, Mitsubishi) for 45 seconds at 4000 rpm and an acceleration of 400 rpm. Samples were stored at room temperature until e-beam exposure.

Electron-Beam Direct-Write Patterning

The PDMS substrates were patterned by e-beam exposure using a scanning electron microscope (FEI XL 30 Sirion) equipped with a Nabity NPGS pattern generator. A 1 $mm^2$ area consisting of an array of spots with diameters ranging from 100 nm to 2 µM were written onto the substrate surface at doses from 500-4,000 µC/cm$^2$, an accelerating voltage of 30 kV and a beam current of approximately 2.5 nanoamperes. Substrates were cleared of AquaSAVE in deionized water three times for 5 minutes each and allowed to air dry for 30 min.

Topographical control substrates were also fabricated by PDMS casting onto directly e-beam written samples to create negative shims. Briefly, e-beam written samples were coated with a silanized monolayer of 99.9% hexamethyldisilazane (Sigma-Aldrich) and the patterned area isolated with a glass cloning-ring. PDMS with a base:accelerator ratio of 5:1 was introduced into the cloning ring and allowed to cure overnight at room temperature. The inverse cloning-ring/PDMS shim was subsequently removed from the direct e-beam written pattern and coated with an anti-adhesive hexamethyldisilazane layer as above. Topographical PDMS substrates prepared as above were imprinted with the PDMS shim overnight to yield topographically yet non-rigidity modified PDMS substrates.

Cell Culture

Substrates were sterilized by successive rinsing in 70% ethanol 3 times for 5 seconds each, followed by phosphate-buffered saline solution (PBS) 3 times for 5 seconds each. Immortalized human mesenchymal stem cells (hMSCs) derived from human bone marrow aspirates were stably transduced by a retroviral vector containing the gene for the catalytic subunit of human telomerase (hTERT). Cells were expanded to passage following 5 weeks of culture and subsequently trypsinized in TrypLE Express dissociation medium (Invitrogen) and seeded onto untreated experimental and planar control tissue culture plates at a density of 1×10$^4$ cells per sample in 1 mL of complete medium. Cells were maintained at 37° C. with a 5% $CO_2$ atmosphere in Dulbecco's modified Eagle's medium (Gibco) supplemented with 10% fetal bovine serum (Gibco), 1% 1-glutamine and 100 IU mg$^{-1}$ penicillin/streptomycin (Invitrogen).

Fluorescent Labeling

Following 24 hours culture on experimental and control substrates, the hMSC cultures were fixed in 4% paraformaldehyde in phosphate-buffered saline solution (PBS), with 1% sucrose at 37° C. for 5 min. Once fixed, the samples were washed with PBS. Samples were permeabilized with buffered 0.5% Triton X-1.00 (10.3 g sucrose, 0.292 g NaCl, 0.06 g $MgCl_2$, 0.476 g [4-(2-hydroxyethyl)-1-piperazineethanesulfonic acid] (HEPES), 0.5 mL Triton X-100, in 100 mL water, pH 7.2) at 4° C. for 5 min. Nonspecific binding sites were blocked with 1% bovine serum albumin (BSA) in PBS at 37° C. for 15 min and subsequently incubated for 2 h with anti-paxillin monoclonal anti-human IgG raised in mouse, (1:200, (B.D Biosciences, Sparks, Md.). Nonspecific charges (e.g. remaining aldehyde) were neutralized with 0.5% Tween 20/PBS three times for 5 min each to minimize background labeling. A secondary, Fluorescein isothiocyanate-conjugated antibody was added, in 1% BSA/PBS, (1:50, Vector Laboratories, Burlingame, Calif.) at 4° C. for 1 h and simultaneously, rhodamine-conjugated phalloidin was added for the duration of this incubation (1:50, Molecular Probes, OR). Substrates were given a final wash in PBS 3 times for 5 min each. Samples were mounted in Vectorshield mounting medium for fluorescence (Vector Laboratories, Burlingame, Calif.). Cell-substrate and cell-cell interaction were examined by scanning confocal microscopy on a stage maintained at 37° C. (live cell imaging). Imaging was performed on an LSM 700 scanning laser confocal microscope with an argon-ion laser (wavelengths 405; 488; 555; 639 nm) fitted with a Zeiss 100× α-PLAN Apochromat objective with a numerical aperture of 1.57 and with ZEN software (Carl Zeiss).

Time-Lapse Videomicroscopy

Time-lapse studies were performed. Briefly, MSCs were seeded onto patterned and control PDMS substrata and incubated for 1 hour to allow cells to adhere. Cell media was subsequently removed and cells cultured in $CO_2$ independent medium (Gibco) supplemented with 10% fetal bovine serum, 1% 1-glutamine and 100 IU mg$^{-1}$ penicillin/streptomycin (Invitrogen). The substrates were sandwiched to an aluminum microscope slide with vacuum grease. Time-lapse micrographs were recorded with a 20×, 0.7 NA air objective (Olympus) through a cooled CCD camera CoolSNAP HQ (Roper Scientific Inc.) using Simple PCI software (Compix Inc.). Images were captured via differential interference contrast (DIC) microscopy every 5 minutes.

Image Analysis

All images were analyzed using ImageJ (National Institutes of Health). Image stacks consisted of 2-3 planes spaced by 0.40 µm which were rendered using standard deviation image intensity to produce a single image of the ventral cell surface. Focal adhesions were analyzed in cells from three separate experiments (20 cells each). Focal adhesion and exposed spot colocalization was analyzed by Manders' method with the JACoP plugin as described in Bolte et al., "A guided tour into subcellular colocalization analysis in light microscopy," *J. Microsc*, 224, 213-232 (2006), incorporated herein by reference in its entirety. Manders' overlap coefficient is based on the Pearson's correlation coefficient with average intensity values being taken out of the mathematical expression, as described in Manders et al., "Dynamics of three-dimensional replication patterns during the S-phase, analysed by double labelling of DNA and confocal microscopy," *J. Cell Sci.* 103 (Pt. 3), 857-862 (1992). This coefficient will vary from 0 to 1, the former corresponding to non-overlapping images and the latter reflecting 100% co-localization between both images. Therefore, M1 (or M2) determined the proportion of the fluorescent paxillin signal coincident with the DIC signal of the substrate over its total intensity, given as the following: $k_1 = (\Sigma_i (A_{i,coloc}))/(\Sigma_i A_i)$ & $k_2 = (\Sigma_i (B_{i,coloc}))/(\Sigma_i B_i)$ With $A_{i,\,coloc}$ being $A_i$ if $B_i > 0$ and 0 if $B_i = 0$; and $B_{i,\,coloc}$ being $B_i$ if $A_i > 0$ and 0 if $A_i = 0$. Fluorescence intensity of focal adhesions was performed on pixels with a colocalization value of 1 relative to pixels with a colocalization value of 0. And plotted with the ImageJ plot profile function. Live-cell analysis of cell motility was performed with the ImageJ plugin MTrackJ.

Surface Characterization

Monte Carlo simulations of electron trajectory in PDMS were conducted with Casino software. Surface physical modification was characterized by nanoindentation, optical profilometry and scanning electron microscopy measurements. Chemical modification was analyzed by water contact angle, angle, X-ray photoelectron spectroscopy (XPS) and confocal laser scanning microscopy measurements. Planar control materials were also subjected to a plasma treatment as described above in the section labeled "Substrate Fabrication."

Nanoindentation

An Agilent G200 nanoindenter Dynamic Contact Module (DCM) head was used to investigate the dynamic modulus at 110 Hz. This frequency is sufficiently close to the natural frequency of the DCM to benefit from increased sensitivity in the measurements. A diamond flat-punch indenter tip of radius 76.4 µm was oscillated at 110 Hz as the nanoindenter head approached the sample. Once contact with the surface of the PDMS was determined, the DCM head maintained a constant load and deflects the springs 1.5 μm. The tip remained in contact with the PDMS and oscillated approximately 500 nm, recording the amplitude and phase of the force and displacement of the embedded tip.

Surface Morphology

A Surface morphological assay was performed with a Veeco Wyko NT9100 optical profiler with a 50× objective. Prior to imaging, samples were sputter-coated with a 12 nm layer of Au at 10 mA and 0.1 mbar using a Cressington 108 sputter coater (Cressington, UK).

Electron Micrographs

Electron micrographs were obtained with a Hitachi S-4700 field-emission scanning electron microscope (FE-SEM) fitted with an Autrata yttrium aluminum garnet (YAG) backscattered electron scintillator-type detector. The images were taken in secondary electron mode, with accelerating voltages between 2 and 5 kV. Images were taken with an emission current of 20 μA, an aperture of 100 μm (apt1) and working distances of 10-12 mm.

Contact Angle

Contact angle measurements were carried out at room temperature using 8 μl water droplets with a model 100_00 contact angle goniometer (Raine-Hart, Inc.). Values were averages of measurements on more than three different samples at more than three different locations on each sample.

X-Ray Spectroscopy

X-ray photoelectron spectroscopy (XPS) spectra were recorded with PHI 5500 model spectrometer equipped with a Al K monochromator X-ray source run at 15 kV and 23.3 mA, a hemispherical electron energy analyzer and a multichannel detector. The test chamber pressure was maintained below $2 \times 10^{-9}$ Torr during the spectrum acquisition. Low energy electron flood gun was used to neutralize possible surface charging. The XPS binding energy (BE) was internally referenced to aliphatic main C 1s peak (BE=284.6 eV). Survey spectrum was acquired at an analyzer pass energy of 93.9 eV and BE resolution of 0.8 eV, while the high resolution spectrum was acquired with a pass energy of 23.5 eV and BE resolution 0.05 eV. Angle-dependent XPS was performed by rotating the sample holder to the desired take-off angle (the angle between the surface normal and the detector) through a motor. Spectrum was fitted by a Guassian-Lorentz (BE) was internally referenced to aliphatic main C 1s peak function after subtracting a striped background using the PHI data processing software package under the constraint of setting reasonable BE shift and characteristic full width at high maximum (FWHM) range. Atomic concentration was calculated by normalization of the peak area to the elemental sensitivity factor data provided by PHI database.

Fibronectin Adsorption

Surface adsorption of fibronectin was analyzed by fluorescence microscopy. Human fibronectin (Sigma Aldrich) was conjugated directly to Alexa Fluor 488 (Invitrogen) by protein dialysis according to manufacturer's instructions (Thermo Scientific). Exposed substrates were prepared as above and immersed in PBS containing 0.5 μg/ml fluorescent fibronectin. Samples were coated for 18 hours before being washed in PBS 3 times for 5 minutes each and mounted for microscopy.

Statistical Analysis

All statistical analysis were performed with SPSS Statistics software 20 (IBM, USA). Data are expressed as mean±SEM with * and ** indicating a 95% and 99.5% confidence interval respectively. ANOVA was used to determine statistical significance followed by post hoc Bonferoni's multiple test correction to determine which groups were statistically different.

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a molding system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented, at least in part. Some examples can include a computer-readable medium or machine-readable medium encoded with instructions operable to configure an electronic device to perform methods or method steps as described in the above examples. An implementation of such methods or method steps can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Although the invention has been described with reference to exemplary embodiments, workers skilled in the art will recognize that changes may be made in form and detail without departing from the spirit and scope of the invention.

What is claimed is:

1. A method for fabricating a substrate, the method comprising:
   forming a substrate of an elastomer, the substrate having a substrate surface; and
   exposing one or more selected regions of the substrate surface to an energy source, the energy source configured to modify a rigidity of the one or more selected regions,
   wherein the one or more selected regions form a specified pattern on the substrate surface, and wherein exposing the one or more selected regions to the energy source to modify the rigidity of the one or more selected regions forms a rigidity pattern on the substrate surface corresponding to the specified pattern, and
   wherein the specified pattern is selected so that the rigidity pattern provides for a differential functional response from cells cultured upon the rigidity pattern.

2. The method according to claim 1, wherein the energy source comprises at least one of a focused electron beam or deep ultraviolet light.

3. The method according to claim 1, wherein the energy source initiates cross-linking of the elastomer in order to increase rigidity of the elastomer in the one or more selected regions.

4. The method according to claim 1, wherein the elastomer comprises poly(dimethylsiloxane) or a poly(dimethylsiloxane)-based polymer.

5. The method according to claim 1, wherein each of the one or more selected regions include at least one of microscale features or nanoscale features.

6. The method according to claim 1, wherein forming the substrate comprises forming the substrate surface to have three-dimensional structures within the one or more selected regions, and wherein exposing the one or more selected regions to the energy source comprises locally modifying a rigidity of the three-dimensional structures.

7. The method according to claim 1, wherein the differential functional response comprises at least one of: differential focal adhesion of the cells to the substrate surface; differential cell differentiation of the cells; differential immune response; or differential growth of the cells.

8. The method according to claim 1, wherein the cells comprise at least one of stem cells, T-cells, cancer cells, nerve cells, osteoblasts, and muscle cells.

9. The method according to claim 1, wherein the rigidity pattern comprises a repeating feature.

10. The method according to claim 9, wherein the repeating feature includes a lateral dimension that is greater than or equal to 250 nanometers.

11. The method according to claim 9, wherein the repeating feature includes a lateral dimension that is less than or equal to 250 nanometers.

12. The method according to claim 9, wherein the repeating feature includes spots.

* * * * *